United States Patent [19]
Peters et al.

[11] Patent Number: 5,378,238
[45] Date of Patent: Jan. 3, 1995

[54] INNERLESS DILATATION CATHETER WITH BALLOON STRETCH OR MANUAL VALVE

[75] Inventors: Jeffrey J. Peters, Golden Valley; Robert M. Vidlund, Eden Prairie, both of Minn.; Michelle Arney, Menlo Park, Calif.

[73] Assignee: SciMed Life Systems, Inc., Maple Grove, Minn.

[21] Appl. No.: 73,326

[22] Filed: Jun. 8, 1993

Related U.S. Application Data

[63] Continuation-in-part of Ser. No. 776,559, Oct. 15, 1991, Pat. No. 5,217,434.

[51] Int. Cl.6 .................. A61M 29/00; A61M 5/00
[52] U.S. Cl. ................... 604/99; 604/249; 606/192
[58] Field of Search ................... 604/96–103, 604/246, 249; 606/192–196; 600/18

[56] References Cited

U.S. PATENT DOCUMENTS

| | | | |
|---|---|---|---|
| 3,331,371 | 7/1967 | Rocchi et al. | 604/96 |
| 3,402,717 | 9/1968 | Doherty | 604/99 |
| 4,130,119 | 12/1978 | Sessions et al. | 604/99 X |
| 4,413,989 | 11/1983 | Schjeldahl et al. | 604/96 |
| 4,572,186 | 2/1986 | Gould et al. | 604/99 X |
| 4,606,347 | 8/1986 | Fogarty et al. | |
| 4,646,742 | 3/1987 | Packard et al. | 606/194 |
| 4,715,378 | 12/1987 | Pope, Jr. et al. | 604/96 X |
| 4,813,934 | 3/1989 | Engelson et al. | 604/99 |
| 4,848,344 | 7/1989 | Sos et al. | |
| 4,932,959 | 6/1990 | Horzewski et al. | 606/194 |
| 5,032,113 | 7/1991 | Burns | 604/96 |
| 5,035,705 | 7/1991 | Burns | 606/194 |
| 5,045,061 | 9/1991 | Seifert et al. | 604/96 |
| 5,059,176 | 10/1991 | Winters | 604/96 |
| 5,078,681 | 1/1992 | Kawashima | 604/53 |
| 5,085,636 | 2/1992 | Burns | 604/99 |
| 5,135,494 | 8/1992 | Engelson et al. | 604/99 |
| 5,141,518 | 8/1992 | Hess et al. | 606/194 |
| 5,171,221 | 12/1992 | Samson | 604/96 |
| 5,171,298 | 12/1992 | Walker et al. | 604/96 |
| 5,176,698 | 1/1993 | Burns et al. | 606/192 |
| 5,181,921 | 1/1993 | Makita et al. | 606/195 |
| 5,192,295 | 3/1993 | Danforth et al. | 606/194 |
| 5,207,229 | 5/1993 | Winters | 128/772 |
| 5,209,728 | 5/1993 | Kraus et al. | 604/96 |
| 5,221,260 | 6/1993 | Burns et al. | 604/99 |
| 5,246,420 | 9/1993 | Kraus et al. | 604/95 |
| 5,256,144 | 10/1993 | Kraus et al. | 604/96 |
| 5,259,839 | 4/1993 | Burns | 604/99 |

FOREIGN PATENT DOCUMENTS

| | | |
|---|---|---|
| 0486157A2 | 10/1991 | European Pat. Off. |
| 3528876A1 | 8/1985 | Germany |
| WO92/00775 | 1/1992 | WIPO |
| WO92/13589 | 8/1992 | WIPO |
| WO92/19311 | 11/1992 | WIPO |

*Primary Examiner*—John D. Yasko
*Assistant Examiner*—Adam J. Cermak
*Attorney, Agent, or Firm*—Nawrocki, Rooney & Sivertson

[57] ABSTRACT

An innerless dilatation balloon catheter uses a balloon 22 which is longitudinally compliant so that it elongates as it is inflated. The catheter 10 includes a valve 30 which is responsive to elongation of the balloon 2 for effectively blocking fluid flow through a lumen extension 24, 26 through which the guide wire 12 passes. The valve 30 allows the guide wire 12 to move freely when the balloon 22 is deflated.

16 Claims, 4 Drawing Sheets

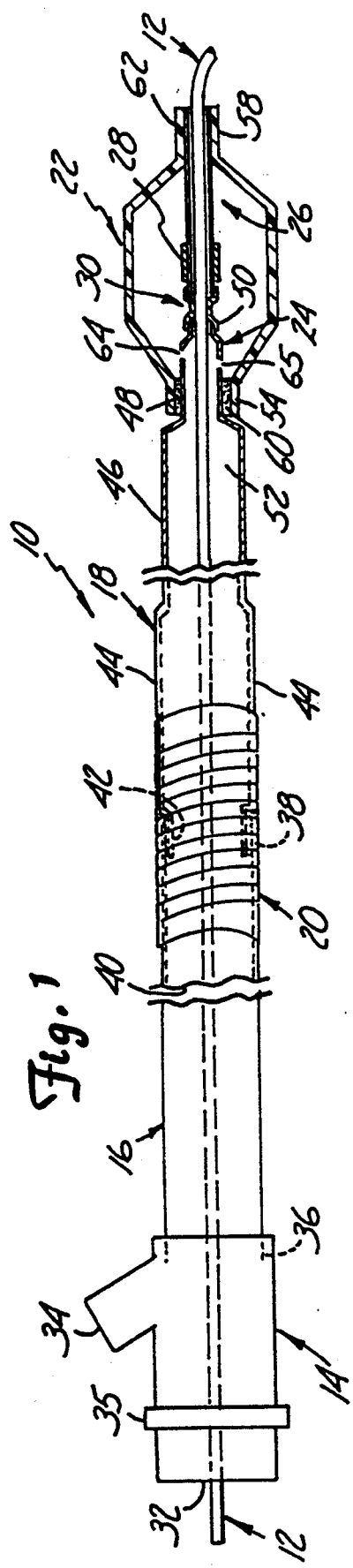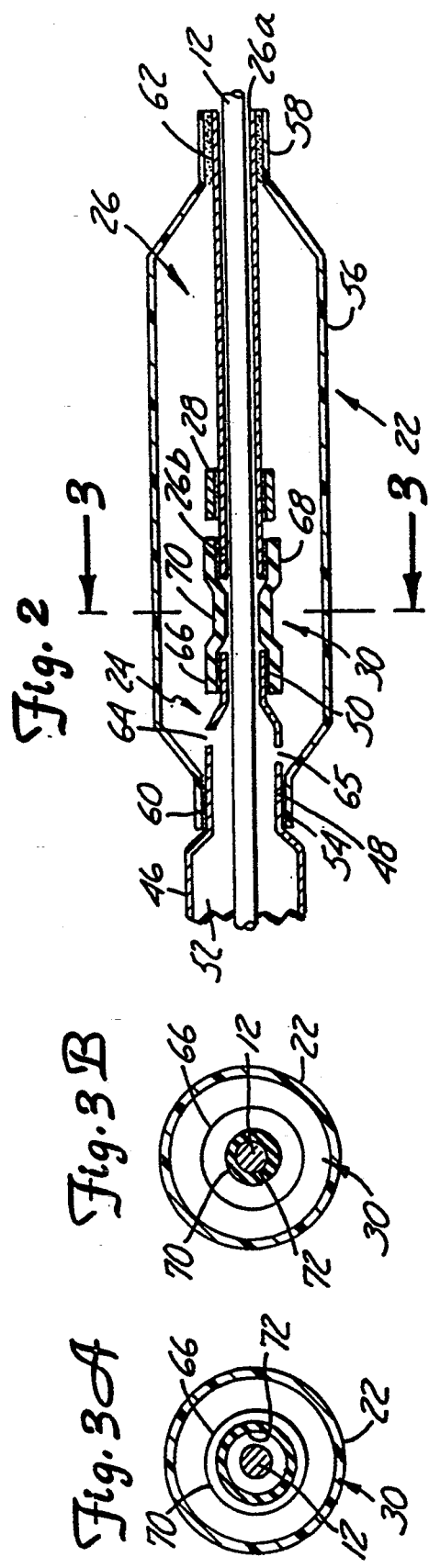

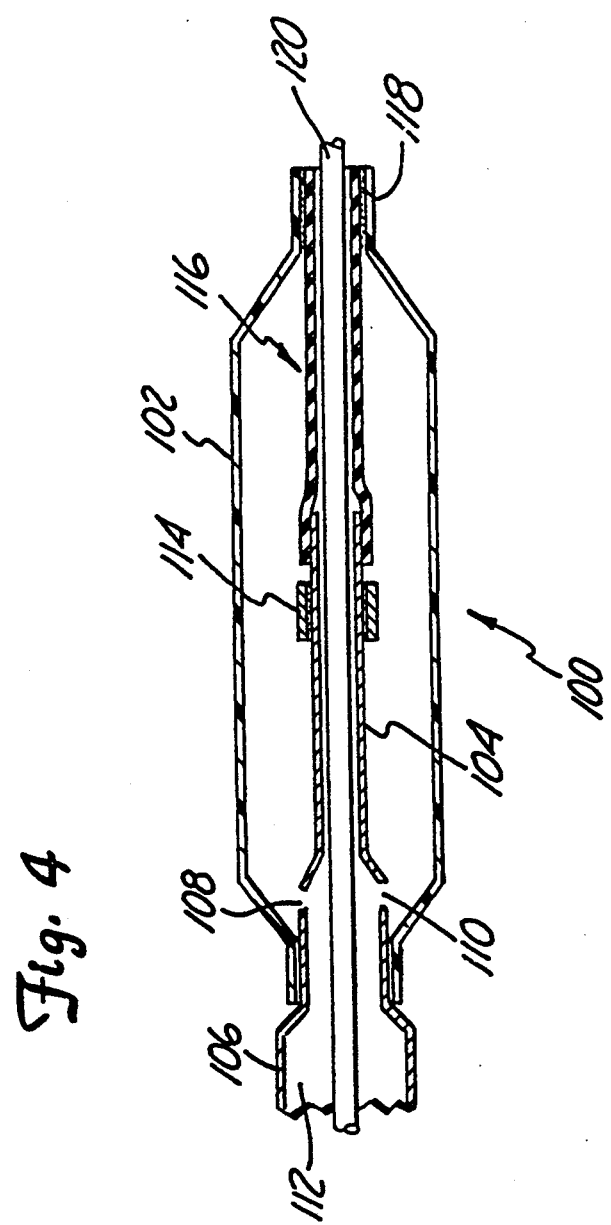

INNERLESS DILATATION CATHETER WITH BALLOON STRETCH OR MANUAL VALVE

CROSS-REFERENCE TO RELATED APPLICATIONS

This is a continuation-in-part of U.S. patent application No. 07/776,559, filed Oct. 15, 1991, now U.S. Pat. No. 5,217,434, for INNERLESS DILATION CATHETER WITH BALLOON STRETCH VALVE, and assigned to the assignee of this invention.

BACKGROUND OF THE INVENTION

The present invention relates to angioplasty. In particular, the present invention relates to an innerless dilation balloon catheter.

Angioplasty has gained wide acceptance in recent years as an efficient and effective method for treating vascular diseases. In particular, angioplasty is widely used for opening stenoses in coronary arteries. It is also used for treatment of stenoses an other parts of the vascular system.

A common form of angioplasty makes use of a dilatation catheter which has an inflatable balloon its distal end. With the aid of fluoroscopy, a physician guides the catheter through the vascular system until the balloon is positioned across the stenosis. The balloon is then inflated by applying fluid pressure through an inflation lumen to the balloon. Inflation of the balloon causes stretching of the artery and pressing of the stenosis-causing lesion into the artery wall to reestablish acceptable blood flow through the artery.

Dilatation catheters can generally be divided into those which are fed over a guide wire (i.e., "over-the-wire-catheters) and those catheters which serve as their own guide wire (i.e., "fixed-wire" catheters). Both types of catheters have advantages and disadvantages.

Innerless dilatation balloon catheters have been developed in an attempt to obtain some of the advantages of a fixed-wire catheter while still retaining the advantages of an over-the-wire catheter. These innerless catheters feature a shaft having a single lumen which acts as both an inflation lumen and a guide wire lumen. A lumen extension extends through the balloon, which is mounted on the distal end of the shaft. The shaft lumen is in fluid communication with the interior of the balloon. The guide wire extends through the shaft lumen, the lumen extension and out the distal end of the balloon.

Examples of innerless dilatation balloon catheters are shown in U.S. Pat. Nos. 5,032,113 and 5,035,705 by Matthew M. Burns.

One consideration in the successful design of any innerless dilatation catheter is that during balloon inflation the inflation fluid must be permitted to flow from the shaft lumen to the interior of the balloon, without substantial leakage of inflation fluid through the lumen extension and out the distal end of the catheter. Similarly, during balloon deflation, blood must not be drawn into the catheter through the lumen extension to such an extent that the balloon will not deflate.

SUMMARY OF THE INVENTION

The present invention is an innerless balloon catheter which includes a shaft with a lumen, a balloon carried at the distal end of the shaft, and a lumen extension which extends through the interior of the balloon and which is an extension of the lumen of shaft to provide a passage for a guide wire. The innerless catheter of the present invention uses, in a first embodiment, a balloon which is longitudinally compliant so that it increases in length as it is inflated. The catheter also includes a valve which is responsive to the length of the balloon. The valve permits free traversal movement of the guide wire from the shaft lumen through the lumen extension when the balloon is deflated. As the balloon is inflated, it stretches axially and increases in length. The valve correspondingly constricts as it stretches to provide a fluid restriction around the guide wire to block fluid flow through the lumen extension.

In a second embodiment, instead of a longitudinally compliant balloon operating the valves a core wire is placed in connection with the valves and is manually operable to move the valves to the desired sealing positions during inflation and deflation of the balloon.

In a first preferred embodiment, the innerless catheter of the present invention includes a two-part lumen extension. The proximal part of the lumen extension is connected to the shaft and provides a flow passage between the shaft lumen and the interior of the balloon. The proximal part of the lumen extension is bonded to a proximal end of the balloon. The distal part of the lumen extension, which extends through a portion of the interior of the balloon, is an inner tube, generally rigid along its axis, having a distal end connected to a distal end of the balloon. In this embodiment, the valve is a stretchable and elastic tube which is connected between the proximal and distal parts of the lumen extension. As the balloon is inflated and stretches axially, the proximal and distal parts of the lumen extension move apart, which coincidentally causes the stretchable tube to stretch axially. The stretchable tube returns to its unstretched state when the balloon is deflated thereby allowing free movement of the guide wire. The stretchable tube has a first inner and outer diameter when the balloon is deflected and has a second, smaller inner and outer diameter when the balloon is inflated and the stretchable tube is stretched. The inner diameter of the stretchable tube valve in its stretched state approximates an outer diameter of the guide wire which extends through the shaft lumen and lumen extension. This results in an effective seal between the shaft lumen and guide wire which prevents leakage of inflation fluid out of the distal end of the catheter.

In a second preferred embodiment, the innerless catheter of the present invention also includes a two-part lumen extension. The proximal lumen extension floats within the distal end of the main shaft lumen and the proximal end of the balloon. It provides a lumen for the guide wire to pass through. Preferably, the main shaft is of a co-braided construction. The distal lumen extension, which extends through a portion of the interior of the balloon, is an inner tube, generally rigid along its axis, having a distal end connected to a distal end of the balloon. In this embodiment, one part of the valve is a ring seal connected by a core wire to a manual actuator available to the operator. When the operator moves the core wire in the distal direction, the ring seal abuts the wall of the shaft to prevent fluid and especially blood from flowing into the balloon. This is important, because the radiopacity of the blood is sufficiently low as to render monitoring of the inflation process difficult using normal radiological techniques.

The other portion of the valve of this second embodiment is a stretchable elastomer tube which is connected between the proximal and distal lumen extensions. As the operator moves the core wire in the proximal direction, the proximal and distal lumen extensions move apart, which causes the elastomer tube to stretch axially. The elastomer tube returns to its unstretched state when the core wire is returned to its distal position thereby releasing the seal on the guide wire. The elastomer tube has a first inner and outer diameter until the core wire is moved toward the proximal end of the catheter, when it takes on a second, smaller inner and outer diameter because the elastomer tube is stretched. The inner diameter of the stretchable tube valve in its stretched state approximates an outer diameter of the guide wire which extends through the shaft lumen and lumen extension. This results in an effective seal between the shaft lumen and guide wire which prevents leakage of inflation fluid out of the distal end of the catheter when the balloon is inflated, and prevents blood from entering when the balloon in deflated under a vacuum. The inner diameter of the valve in its relaxed state provides sufficient clearance to prevent contact with the guide wire.

BRIEF DESCRIPTION OF THE DRAWINGS

FIG. 1 is a partial sectional view of a preferred embodiment of the innerless dilatation catheter of the present invention.

FIG. 2 is a partial sectional view showing in further detail the distal portion of the innerless dilatation catheter of FIG. 1.

FIG. 3A is a sectional view of the innerless dilatation catheter taken on line 3—3 of FIG. 2 with an open valve.

FIG. 3B is a sectional view of the innerless dilatation catheter taken on line 3—3 of FIG. 2 with a closed valve.

FIG. 4 is a partial sectional view showing another embodiment of the present invention.

DETAILED DESCRIPTION OF THE PREFERRED EMBODIMENTS

Figure 5:
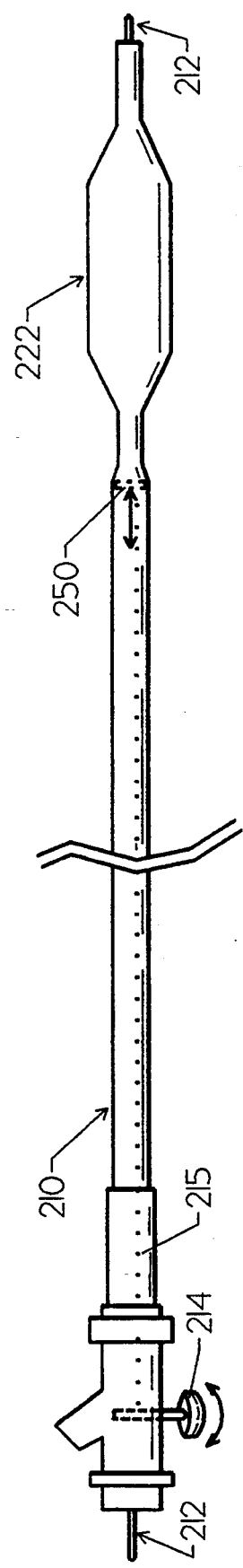
FIG. 5 is a plan view of yet another embodiment of this invention.

FIG. 1 shows dilatation catheter 10 and guide wire 12, which are used to perform angioplasty procedures. Dilatation catheter 10 includes manifold 14, proximal shaft 16, distal shaft 18, strain relief 20, balloon 22, proximal lumen extension 24, distal lumen extension 26, marker band 28, and stretch responsive valve 30.

Manifold 14 is located at the proximal end of the dilatation catheter 10. Manifold 14 includes port 32 (through which guide wire 12 passes), balloon port 34 (through which inflation fluid is provided to and withdrawn from balloon 22) and manifold valve 35.

Proximal shaft 16 is a single lumen tube having its proximal end 36 connected to manifold 14, and its distal end 38 connected to distal shaft 18. Shaft lumen 40 extends from proximal end 36 to distal end 38 of shaft 16. Lumen 40 is in fluid communication with balloon port 34 and port 32 of manifold 14, and also provides a passage for guide wire 12.

Distal shaft 18 includes proximal neck section 42, shaft sections 44 and 46, bond neck section 48, and valve neck section 50. Proximal neck section 42 is bonded to distal end 38 of proximal shaft 16.

Strain relief 20, which is preferably a wrapped stainless steel ribbon covered by a thin heat-shrunk polymer sleeve, fits over the bond between distal portion of shaft 16 and the proximal portion of shaft 18. Strain relief 20 provides additional strength at the bond between shafts 16 and 18, particularly when tension is applied to the bond.

Shaft section 44 of distal shaft 18 has an outer diameter which is equal to or slightly less than the outer diameter of proximal shaft 16. In the embodiment shown in FIG. 1, shaft section 46 is positioned intermediate to shaft section 44 and bond neck section 48. Shaft section 46 has a reduced outer and inner diameter with respect to section 44 and, in the preferred embodiment, has a greater flexibility than proximal shaft 16 and shaft section 44 of distal shaft 18.

Bond neck section 48 has a reduced outer and inner diameter with respect to shaft section 46. Valve neck section 50 has a reduced outer and inner diameter with respect to bond neck section 48. Bond neck section 48 and valve neck section 50 together form proximal lumen extension 24. Distal shaft 18 has a lumen 52 which is aligned with lumen 40 of proximal shaft 16.

Balloon 22 includes proximal balloon waist 54, main balloon body 56, and distal end section 58. Proximal balloon waist 54 is bonded to bond neck section 48 by adhesive 60. Similarly, distal end section 58 of balloon 22 is bonded by adhesive 62 to the distal end of distal lumen extension 26.

As shown in FIG. 1, guide wire 12 extends from port 32 of manifold 14, through shaft lumens 40 and 52, through proximal lumen extension 24 (formed by bond neck section 48 and valve neck section 50), through stretch response valve 30, through distal lumen extension 26 and out the distal end 58 of balloon 22 of catheter 10.

Inflation of balloon 22 is effected by passing fluid (not shown) through lumens 40 and 52 and vent holes 64 and 65 in proximal lumen extension 24. The fluid flow resistance through vent holes 64 and 65 is preferably less than the fluid resistance between guide wire 12 and the remainder of the lumen extension distal to vent holes 64 and 65. In this way, it is possible to supply inflation fluid under pressure to the interior of balloon 22 through the same lumen 40, 52 used by guide wire 12.

Referring to FIGS. 1 and 2, the present invention further limits the flow of fluid in either direction between lumen 52 and the distal end of catheter 10 by the action of stretch responsive valve 30 during balloon inflation. The present invention takes advantage of a characteristic of certain balloon material: a longitudinal compliance of balloon 22. In other words, as balloon 22 is inflated, it tends to elongate. This causes the distance between proximal balloon waist 54 and distal end section 58 to increase as balloon 22 is inflated. Because proximal balloon waist 54 is secured by adhesive 60 to bond neck section 48, and distal end section 58 is attached by adhesive 62 to a distal end 26A of distal lumen extension 26 tends to move away from valve neck section 50 as the balloon 22 is inflated.

As best shown in FIG. 2, stretch responsive valve 30 is preferably a stretchable tube having a proximal section 66 attached to valve neck section 50, and a distal section 68 attached to proximal end 26b of distal lumen extension 26. Intermediate section 70 of valve 30 is located in the gap between valve neck 50 and distal lumen extension 26.

Elongation of balloon 22 due to its inflation causes valve 30 to stretch. As valve 30 is stretched, the length of intermediate section 70 increases and the inner diameter of intermediate section 70 correspondingly decreases. Consequently, stretching valve 30 effectively decreases the inner diameter of a portion of the lumen extension. Preferably the amount of stretching of balloon 22, and the dimensions of valve 30 and guide wire 12 are determined while balloon 22 is inflated to pressures in its working range (approximately 0 to 18 atmospheres); the inner wall of valve 30 should approximate the outer surface of guide wire 12 and substantially block fluid flow in either direction through valve 30.

At low inflation pressures of balloon 22, valve 30 stretches sufficiently to effect the constricting action of valve 30 and restrict fluid flow between lumen 52 and distal end 26a of distal lumen extension 26.

To achieve this valve action, proximal lumen extension 26 (formed by bond neck section 48 and valve neck section 50) and distal lumen extension 26 must be sufficiently rigid to transmit force to valve 30. In a preferred embodiment of the present invention, the amount of elongation of balloon 22 in its working range is approximately 0 to 10 millimeters.

In a preferred embodiment of the present invention, balloon 22 is a polyolefin balloon material, such as Surly 8527 from Dupont, which exhibits longitudinal compliance (stretching) during inflation. Proximal balloon waist 54 has an inner diameter of about 0.0262 to 0.0280 inches and an outer diameter of about 0.033 to 0.042 inches maximum depending on the inflated outer diameter of balloon 22. Distal end section 58 of balloon 22 has an inner diameter of about 0.0205 to 0.023 inches. The overall length of balloon 22 is typically between 1 to 4 centimeters. Proximal balloon waist 54 has a length of about 8 millimeters, and distal end section 58 has a length of about 3 millimeters.

Proximal shaft 16 is preferably a polyimide/stainless steel braid composite tube from HV Technologies of Trenton, Ga. with an inner diameter of about 0.0265 inches and an outer diameter of about 0.033 inches. The length of proximal shaft 16 is about 103 centimeters. Alternatively, proximal shaft 16 is made of any other material which provides enough rigidity for good pushability and relatively thin walls.

Strain relief 20 is a 0.001 inch by 0.004 inch stainless steel ribbon which is wrapped around proximal shaft 16 and distal shaft 18 and covered by a heat-shrunk polymer sheath. Strain relief 20 has an outer diameter of about 0.038 inches and a length of about 2.5 centimeters.

In a preferred embodiment of the present invention, distal shaft 18 and distal lumen extension 26 are formed of high density polyethylene tubing and are formed as one piece by a series of necking operations. Distal lumen extension 26 is subsequently severed from valve neck section 50 to create the gap for valve 30.

In this embodiment, proximal neck section 42 has a length of about 4 millimeters, an inside diameter of about 0.021 inches, and an outer diameter of about 0.025 inches. Shaft section 44 has a length of about 9 centimeters, and an inner diameter of about 0.0245 to 0.0270 inches, and an outer diameter of about 0.032 inches.

Shaft section 46 has a length of about 23 centimeters, and inner diameter of about 0.020 to 0.027 inches and an outer diameter of about 0.025 to 0.022 inches. Bond neck section 48 has a length of about 10 millimeters, an outer diamter of about 0.0252 to 0.0257 inches and an inner diamter of about 0.020 to 0.021 inches. Vent holes 64 and 65 are round holes about 0.007 to 0.010 inches to diameter. Vent hole 64 is located about 9.5 millimeters distal to shaft section 46. Vent hole 65 is located about 8.5 millimeters distal to shaft section 46. Vent hole 64 is positioned 180 degrees from vent hole 65 around the circumference of bond neck section 48, as illustrated in FIGS. 1 and 2.

Valve neck section 50 and distal lumen extension 26 have inner diameters of about 0.0155 to 0.016 inches and outer diameters of about 0.019 to 0.020 inches. Valve neck section 50 has a length of about 2.5 millimeters, while distal lumen extension 26 has a length which depends on the size and length of balloon 22.

The reduced diameter sections of dilatation catheter 10, such as valve neck section 50 and distal lumen extension 26, haven become oriented molecularly as a result of the necking down of the high density polyethylene tubing. This provides the additional rigidity in the axial direction necessary to transmit force from proximal balloon waist 54 and distal end section 58 of balloon 22 to valve 30.

In this preferred embodiment, valve 30 is a tube made of a polyurethane, such as Pellethane 2352-70A from Dow Chemical, with an inner diameter of about 0.0145 to 0.0150 inches and a maximum outer diamter of about 0.020 inches. Valve 30 is soaked in alcohol and then stretched over valve neck section 50 and proximal end 26b of distal lumen extension 26. Proximal section 66 and distal section 68 of valve 30 are about 1.5 to 2.0 millimeters in length, while intermediate section 20 is about 1 to 5 millimeters in length in its unstretched state. The total elongation of balloon 22 is about 0 to 10 millimeters.

Marker band 28 is a band of radiopaque metal located on distal lumen extension 26 near proximal end 16b such that marker bank 28 is positioned approximately in the center of balloon 22. Marker band 28 has an inner diameter of about 0.0205 to 0.0210 inches and a wall thickness of about 0.0019 to 0.0020 inches.

Guide wire 12, used in conjunction with catheter 10, has an overall length of about 175 centimeters. The outer diameter of guide wire 12 is about 0.014 inches over the length of the body. The inner surfaces of proximal lumen extension 24, distal lumen extension 26 and valve 30 must be large enough to permit free passage of guide wire 12 when balloon 22 is not inflated, yet be in close enough proximity to guide wire 12 to allow valve 30 to create the desired seal around wire 12 while balloon 22 is in an inflated state.

As shown in FIG. 3A, in an unstretched state, the inner surface 72 of valve 30 is not in contiguous contact with guide wire 12, thereby permitting free passage of guide wire 12 through valve 30. The close proximity of guide wire 12 with inner surface 72 of valve 30 and the inner surfaces of valve neck section 50 and distal lumen extension 26 (not shown) are such that the inflation fluid distal to vent holes 64 and 65 experiences greater flow resistance with respect to the fluid flow resistance through vent holes 64 and 65 shown in FIG. 2. This yields minimal fluid leakage out the distal end of innerless dilatation catheter 10 while balloon 22 is inflating and valve 30 is constricting around guide wire 12 to block fluid flow.

FIG. 3B demonstrates valve 30 in a stretched state where the stretching decreases the inner and outer diameter of valve 30 thereby bringing inner surface 72 of valve 30 in contiguous contact with guide wire 12 and blocking fluid flow through distal lumen extension 26 (not shown).

Other constructions of valve 30 are also possible within the scope of the present invention. For example, the location of valve 30 within balloon 22 may be varied, and the dimensions of valve 30 can be changed. Also, valve 30 could be positioned within the distal portion of shaft 18.

A sectional view of another embodiment of the present invention is shown in FIG. 4. Distal end of catheter 100 with balloon 102 is shown with proximal lumen extension 104 connected to and extending from the distal end of shaft 106. Vent holes 108 and 110 are positioned on proximal lumen extension 104 to permit fluid communication between lumen 112 of shaft 106 and balloon 102. Unlike the embodiment shown in FIG. 3, however, the proximal lumen extension 104 extends to approximately an intermediate location within balloon 102. Marker band 114 is affixed near the distal end of proximal lumen extension 104.

The proximal end of valve 116 is connected to the distal end of proximal lumen extension 104, and the distal end of valve 116 is bonded to distal balloon waist 118. Valve 116 therefore defines the distal lumen extension 26 of FIG. 3. Like valve 30 of FIG. 3, valve 116 is axially compliant when tension is applied during balloon inflation. Other constructions of valve 116 are also possible. For example, valve 116 and distal lumen extension 104 can be incorporated into a single elastic tubular member which has compression strength in the axial direction and flexibility in tension while retaining sufficient elasticity to allow the tubular member to stretch and create a seal around guide wire 120 as balloon 102 inflates and elongates.

Guide wire 120 extends from lumen 112 of shaft 106 through proximal lumen extension 104 and valve 116 (shown in its unstretched state) and out the distal end of catheter 100. As balloon 102 is inflated and elongate, tension is applied to valve 116 thereby causing valve 116 to stretch and reduce its inner and outer diameter along essentially the entire length of valve 116. The inner diameter of a substantial length of valve 116 in a stretched state approximates the outer diameter of guide wire 120 while balloon 102 is inflated. This causes an effective obstruction of lumen 112 which essentially suppresses the flow of inflation fluid out the distal end of catheter 100 while balloon 102 is inflated.

Referring now to FIG. 5, there is shown another preferred embodiment of the apparatus of this invention. A catheter 210 is shown connected at its proximal end to a fluid sealed rotational actuator 214 capable of moving the core wire 215 along the catheter axis in both the distal and proximal directions. The main body of catheter 210 is preferably a proximal shaft of a co-braided construction as is taught in commonly assigned and co-pending U.S. patent application Ser. No. 07/867,164, incorporated herein by reference. A guide wire 212 is shown extending through catheter 210. A balloon 222 is connected to catheter 210 near its distal end. In this embodiment it is not necessary that balloon 222 have the special longitudinal extension qualities described above in the discussion of FIGS. 1–4. A core wire 215 is depicted in shadow lines and is shown connected between actuator 214 and a valve assembly 250. Thus, when actuator 214 is moved axially in the proximal or distal direction, core wire 215 will cause a corresponding movement of valve assembly 250.

Figure 6:
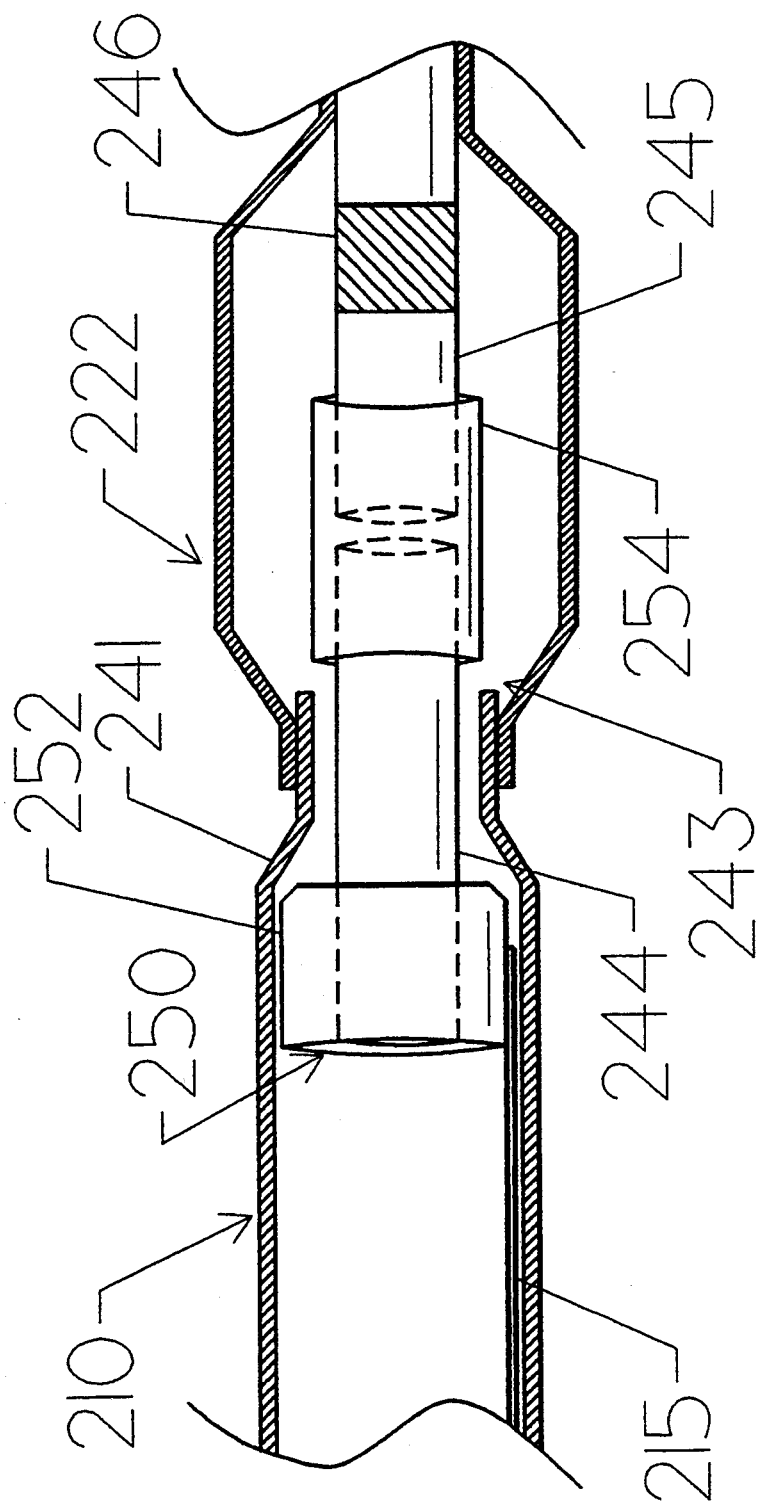
FIG. 6 is a partial sectional view of the embodiment of FIG. 5.

Referring now to FIG. 6, there is shown a portion of the apparatus of FIG. 5, with additional details added. Catheter 210 is shown having a proximal shaft 241 having annuler space 243 to allow fluid flow between the lumen of catheter 210 and the interior of balloon 222. There is also shown proximal extension 244 and distal extension 245 which comprises a pair of spaced rigid tubes. Tubes 244 and 245 pass through balloon 222 and allow a guide wire such as wire 212 of FIG. 5 (not shown in FIG. 6) to pass through the catheter 210, and exit the balloon 222.

In FIG. 6 valve assembly 250 is shown to comprise a first seal 252, preferably a ring seal of stainless steel hypotubing, and another seal 254, preferably an elastomer seal of polyurethane. Seal 254 is mounted to bridge the selected gap between tubes 244 and 245, and is sealingly mounted on tubes 244 and 245. The gap is minimized so as to prevent elastomer tube 254 in its relaxed state from interfering with movement of the guide wire. A marker 246 is shown on tube 245, which serves the same purpose as described above in the discussion of FIGS. 1–4. Core wire 215 is shown connected to seal 252. In this preferred embodiment, wire 215 is preferably stainless steel, and it can be seen to perform a dual purpose; first, wire 215 is connected to actuate valve assembly 250; and second, wire 215 provides axial support, pushability, and axially varying flexibility to catheter 210.

In operation of this second preferred embodiment of FIGS. 5 and 6, assume first that actuator 214 has been moved axially in the distal direction. This movement will be felt through core wire 215 to cause a like movement of assembly 250. When moved in the distal direction, seal 252 will come into sealing contact with proximal shaft 241 thus sealing annuler space 243 and balloon 222 from blood flow from the lumen of catheter 210. Sealing the balloon from the ingress of blood flow prevents the contrast media from being diluted and thus allows the balloon inflation to be visualized radioscopically. When the balloon 222 has reached the desired location in the body, actuator 215 is manually moved toward the proximal end of catheter 210. This has a dual result: first, ring seal 252 is removed from contact with proximal shaft 241 thus allowing the flow of balloon inflation fluid from the lumen of catheter 210, through annular space 243, and into the interior of balloon 222; and, second, proximal extension tube 244 is also moved proximally. This causes seal 254 to stretch, and neck down to a decreased inside diameter within the widened gap between proximal extension tube 244 and distal extension tube 245 such that seal 254 comes into sealing contact with guide wire 212 (not shown in FIG. 6). Thus the central lumen is in sealed fluid communication with the interior of balloon 222 allowing for inflation. This sealing action of seal 254 against the guide wire 212 is similar to that sealing action described above in the discussion of FIGS. 1–4.

Other constructs are also possible within the scope of the preset invention. For example, catheter 10 can also accompany guide wires of different outer diameter (e.g., 0.010, 0.018, and 0.035 inches) and balloons of different inflated diameters. The components of catheter 10 are dimensionally scaled accordingly. Furthermore, the present invention may be used to seal the central lumen to a smaller concentric catheter, such as a guide catheter or smaller diameter dilatation catheter.

Although the present invention has been described with reference to preferred embodiments, workers skilled in the art will recognize that changes may be made in form and detail without departing from the spirit and scope of the invention.

What is claimed is:

1. A balloon catheter assembly comprising:
 a guide wire;
 a shaft having a proximal end, a distal end, and a lumen which extends between the proximal end and the distal end, the guide wire extending through the lumen;
 a balloon carried at the distal end of the shaft, the balloon having an interior which is in fluid communication with the lumen to permit inflation and deflation of the balloon;
 a lumen extension through the interior of the balloon to provide a passage for the guide wire to extend through the balloon;
 a manual valve actuator mounted at the proximal end of said catheter;
 a valve assembly connected to said lumen extension;
 a core wire connected between said valve actuator and said valve assembly; and,
 said valve assembly including seal apparatus responsive to movement of said actuator for blocking fluid flow through the lumen extension during inflation and deflation of the balloon.

2. The balloon catheter of claim 1 wherein the valve assembly comprises a flexible tube including a seal positioned within the interior of the balloon which stretches as said actuator is moved, said flexible tube having an inner surface which defines a portion of the lumen extension and which engages the guide wire to block fluid flow through the lumen extension when said flexible tube is stretched.

3. The balloon catheter of claim 2 wherein the lumen extension includes a proximal portion and a distal portion, the proximal portion being connected to the core wire and in spaced relation to the distal portion connected to a distal end of the balloon.

4. The balloon catheter of claim 3 wherein the flexible seal is mounted to and extends between the proximal portion and the distal portion of the lumen extension.

5. The balloon catheter of claim 1, 2, 3 or 4 wherein the valve assembly further comprises a shaft seal connected to and selectively moveable by said actuator for selectively sealing the shaft lumen from the interior of the balloon.

6. A balloon catheter assembly comprising:
 an inflatable balloon;
 a shaft which carries the inflatable balloon at a distal end of the shaft, the shaft having a lumen therethrough and the lumen being in fluid communication with an interior of the balloon for inflation and deflation of the balloon through the lumen;
 a lumen extension through the balloon, the lumen extension being in fluid communication with the lumen;
 a guide wire movably extending through the lumen and the lumen extension;
 a valve assembly located proximate the lumen extension for selectively limiting fluid flow through the lumen extension during the inflation and deflation of the balloon;
 a valve assembly actuator located proximate the valve assembly; and
 a core wire connected between the actuator and the valve assembly.

7. The balloon catheter assembly of claim 6 wherein the valve assembly comprises resilient means within the lumen extension which surrounds the guide wire within the lumen extension.

8. The balloon catheter assembly of claim 7 wherein the lumen extension includes a pair of tubes in spaced relation, the resilient means comprising a flexible ring generally coaxial with the lumen extension and spanning the space between the pair of tubes.

9. The balloon catheter assembly of claim 8 wherein the flexible ring is responsive to movement of the actuator to decrease its inner diameter in the space between the pair of tubes.

10. In a catheter having a proximal end and a distal end and having a central lumen adapted to receive a concentric guide dement, the improvement comprising:
 (a) a valve near said distal end of said catheter for sealing said central lumen against said concentric guide dement; and
 (b) a mechanical actuator located near said proximal end of said catheter and coupled to said valve such that actuation of said actuator causes opening and closing of said valve.

11. An intravascular device, comprising:
 (a) an elongate shaft with a lumen extending therethrough, the lumen adapted to at least partially slidably receive a guide member;
 (b) a deformable sealing member fixed to the distal end of the elongate shaft; and
 (c) a mechanical actuating member coextending with the elongate shaft, the distal end of the actuating member operatively connected to the sealing member such that when the actuating member is actuated, the sealing member engages a fluid seal between the lumen and the guide member.

12. The intravascular device of claim 11, wherein:
 the deformable sealing member is tubular.

13. The intravascular device of claim 11, further comprising:
 an inflatable balloon connected to the distal end of the elongate shaft and in fluid communication with the lumen.

14. The intravascular device of claim 13, wherein:
 the lumen facilitates the transport of inflation fluid thereby allowing the balloon to be selectively inflated and deflated.

15. The intravascular device of claim 14, further including:
 a fluid path defined by the lumen and the balloon.

16. The intravascular device of claim 15, wherein:
 the fluid path is terminated distally when the sealing member engages the guide member.

* * * * *